(12) United States Patent
Horstmann

(10) Patent No.: US 7,256,040 B2
(45) Date of Patent: Aug. 14, 2007

(54) METHOD AND APPARATUS FOR PREPARING MONOLAYERS OF CELLS

(75) Inventor: Heinz Horstmann, Plankstadt (DE)

(73) Assignee: Leica Mikrosysteme GmbH, Vienna (AT)

( * ) Notice: Subject to any disclaimer, the term of this patent is extended or adjusted under 35 U.S.C. 154(b) by 698 days.

(21) Appl. No.: 10/172,473

(22) Filed: Jun. 14, 2002

(65) Prior Publication Data

US 2003/0003577 A1    Jan. 2, 2003

(30) Foreign Application Priority Data

Jun. 15, 2001 (EP) .................................. 01114433

(51) Int. Cl.
*C12N 5/00* (2006.01)
(52) U.S. Cl. .................... 435/325; 435/1.3; 435/40.51; 435/283.1; 435/307.1; 435/176; 435/172; 435/182; 435/374

(58) Field of Classification Search ................ 435/325, 435/374, 1.3, 40.51, 307.1, 283.1, 176, 177, 435/182
See application file for complete search history.

(56) References Cited

U.S. PATENT DOCUMENTS 4,306,425 A * 12/1981 Sitte et al.

FOREIGN PATENT DOCUMENTS

DE    29 44 464 A   *   5/1981
DE    37 12 531 C   *   5/1988

OTHER PUBLICATIONS

Hernandez-Verdun et al. Biology of the Cell 72 pp. 121-132 1991.*
"Reichert AFS, Automatic Freeze-Substitution-System, according to Sitte and Edelmann" Leica/Reichert Division Brochure 1993.

* cited by examiner

*Primary Examiner*—Leon B Lankford, Jr.
(74) *Attorney, Agent, or Firm*—Simpson & Simpson, PLLC

(57) ABSTRACT

The invention concerns an apparatus for preparing monolayers of cells. The apparatus comprises a container (6) for a cryosubstitution system and an insert (1) for the container, the insert (1) having a surface (1*a*) and a plurality of orifices (3). An SCS (2) together with a cellular monolayer (20) is insertable into each of the orifices (3). The SCS (2) is thus arranged perpendicular to the surface (1*a*) of the insert (1).

4 Claims, 6 Drawing Sheets

METHOD AND APPARATUS FOR PREPARING MONOLAYERS OF CELLS

CROSS REFERENCE TO RELATED APPLICATIONS

This application claims priority of the European patent application 01 114 433.4 which is incorporated by reference herein.

FIELD OF THE INVENTION

The invention concerns a method for preparing monolayers of cells.

The invention furthermore concerns an apparatus for preparing monolayers of cells. In particular, the invention concerns a container for a cryosubstitution system and an insert for the container.

BACKGROUND OF THE INVENTION

According to a method of the existing art (see 1993 Leica brochure of Leica Aktiengesellschaft, Vienna, Austria), it is proposed to perform a cryosubstitution in special flow-through capsules (Reichert™). Embedding of the specimen for producing thin sections is then also accomplished in the same capsules. A method for the preparation of thin sections of cellular monolayers is not presented here. In addition, the container of the specimens for cryosubstitution disclosed in the existing art cannot successfully guarantee the cryosubstitution of cellular monolayers.

SUMMARY OF THE INVENTION

It is the object of the invention to create a method with which cellular monolayers can be prepared in simple fashion, and thereby to make available an efficient way of producing thin sections of the cellular monolayer for subsequent microscopic examination.

The object is achieved by a method comprising the following steps:
culturing a cellular monolayer on at least one SCS;
cooling each SCS together with the cellular monolayer in such a way that the formation of ice crystals in the cells of the monolayer is avoided;
substituting the cellular water in the cells of the monolayer; and
embedding the cellular monolayer together with the SCS in such a way that the cells of the cellular monolayer on the SCS are surrounded by embedding material, and the SCS is substantially free of embedding material.

A further object of the invention is to create an apparatus which allows cellular monolayers to be prepared in such a way that efficient section production for a subsequent microscopic examination can be achieved. Moreover, the apparatus is also intended to ensure efficient utilization of the cellular monolayer for production of the thin sections.

The object is achieved by means of an apparatus for preparing monolayers of cells, which comprises:
a container for a cryosubstitution system,
an insert for the container wherein the insert defines a surface and a plurality of orifices, and
at least one SCS, carrying a cellular monolayer, is insertable into the plurality of orifices so that the SCS is arranged perpendicular to the surface of the insert.

The invention has the advantage that the method according to the present invention makes possible reliable specimen preparation of cellular monolayers. For that purpose, a cellular monolayer is cultured on a sapphire coverslip (SCS). Culturing is performed in a conventional tissue culture dish. The cellular monolayer formed on the SCS is removed from the tissue culture dish. Cooling of each SCS together with the cellular monolayer is then accomplished in such a way that the formation of ice crystals in the cells of the monolayer is avoided. The cooled SCSs are introduced into a suitable apparatus that itself is transferred into a cryosubstitution system (CSS). In the CSS, the cellular water in the cells of the monolayer is substituted with a suitable medium. Lastly, the cellular monolayer together with the SCS is embedded in such a way that the cells of the cellular monolayer on the SCS are surrounded by embedding material, and the SCS is substantially free of embedding material.

The embedding material is cured by irradiation with light of a suitable wavelength. The entire cured block is cooled in such a way that the SCS can be popped off from the embedding material as a result of mechanical stresses.

It is particularly advantageous if the substitution is performed in a CSS, each SCS with the cellular monolayer being introduced into the container using an insert. The container itself is inserted into the CSS, the SCSs being arranged perpendicular to the surface of the insert. The insert possesses a central opening through which, using a hollow needle, the container in the CSS can be filled with an appropriate medium so that substitution of the water in the cells of the cellular monolayer can be performed.

Methanol or acetone, for example, has proven to be a suitable medium for substituting the water in the cells of the cellular monolayer. Additions of uranyl acetate (UA) or $OSO_4$ are used for contrast and to fix the cells.

The apparatus for preparing monolayers of cells proves to be particularly advantageous for the method if it comprises a container for the CSS and if the container itself is equipped with an insert. The insert possesses a plurality of orifices, an SCS together with a cellular monolayer being insertable into each of the orifices in such a way that the SCS is arranged perpendicular to the surface of the insert.

Further advantageous embodiments of the apparatus are evident from the dependent claims.

BRIEF DESCRIPTION OF THE DRAWINGS

The subject matter of the invention is depicted schematically in the drawings and will be described below with reference to the Figures, in which.

DETAILED DESCRIPTION OF THE INVENTION

The monolayer of cells is already present on a sapphire coverslip (SCS). The method for preparing the monolayers of cells is disclosed in the description of FIG. 6. Without raising the temperature of the specimens above −100° C., they are transferred into a cryosubstitution system (CSS). The CSS is not depicted, since it is sufficiently known to anyone skilled in this art.

Figure 1:
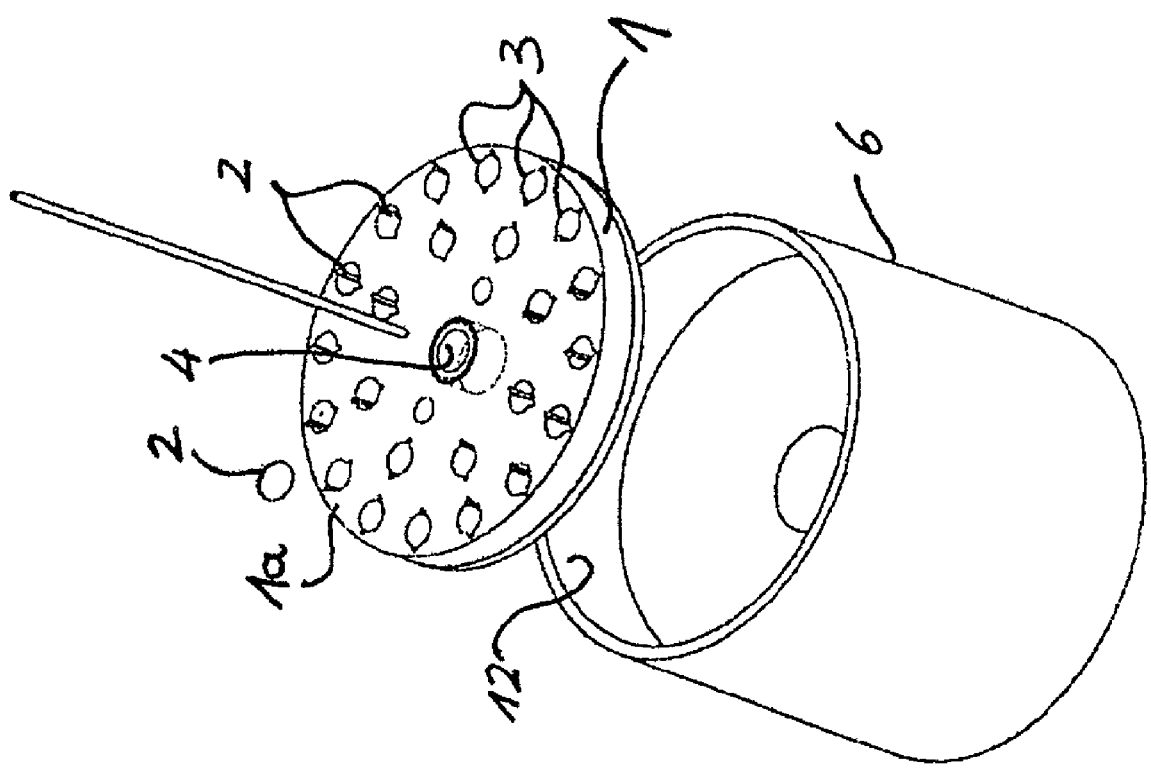
FIG. 1 is a perspective view of the insert for holding the SCSs during substitution.

FIG. 1 depicts an insert 1 that serves to hold SCSs 2 in the CSS. Insert 1 possesses a plurality of orifices 3 which are configured such that SCSs 2 can be inserted perpendicularly (see FIG. 2 for a more detailed depiction of this). SCSs 2, together with cellular monolayer 20, are arranged in insert 1 perpendicular to the latter's surface 1a. A container 6 is provided for the reception of insert 1. Container 6 is in thermal contact with the CSS. Insert 1 is circular in shape, and fits into a receptacle 12 (also circular) that is configured on container 6. A central opening 4, through which a medium can be delivered centrally to container 6, is configured in insert 1. Container 6 is filled with medium by means of a hollow needle 5 until SCSs 2 are immersed. An exchange of media can also take place through this opening 4. Container 6 is in good thermal contact with the temperature-controlled surface of the CSS, so that preselected temperature profiles can also be achieved in the medium that is present in container 6.

Figure 2:
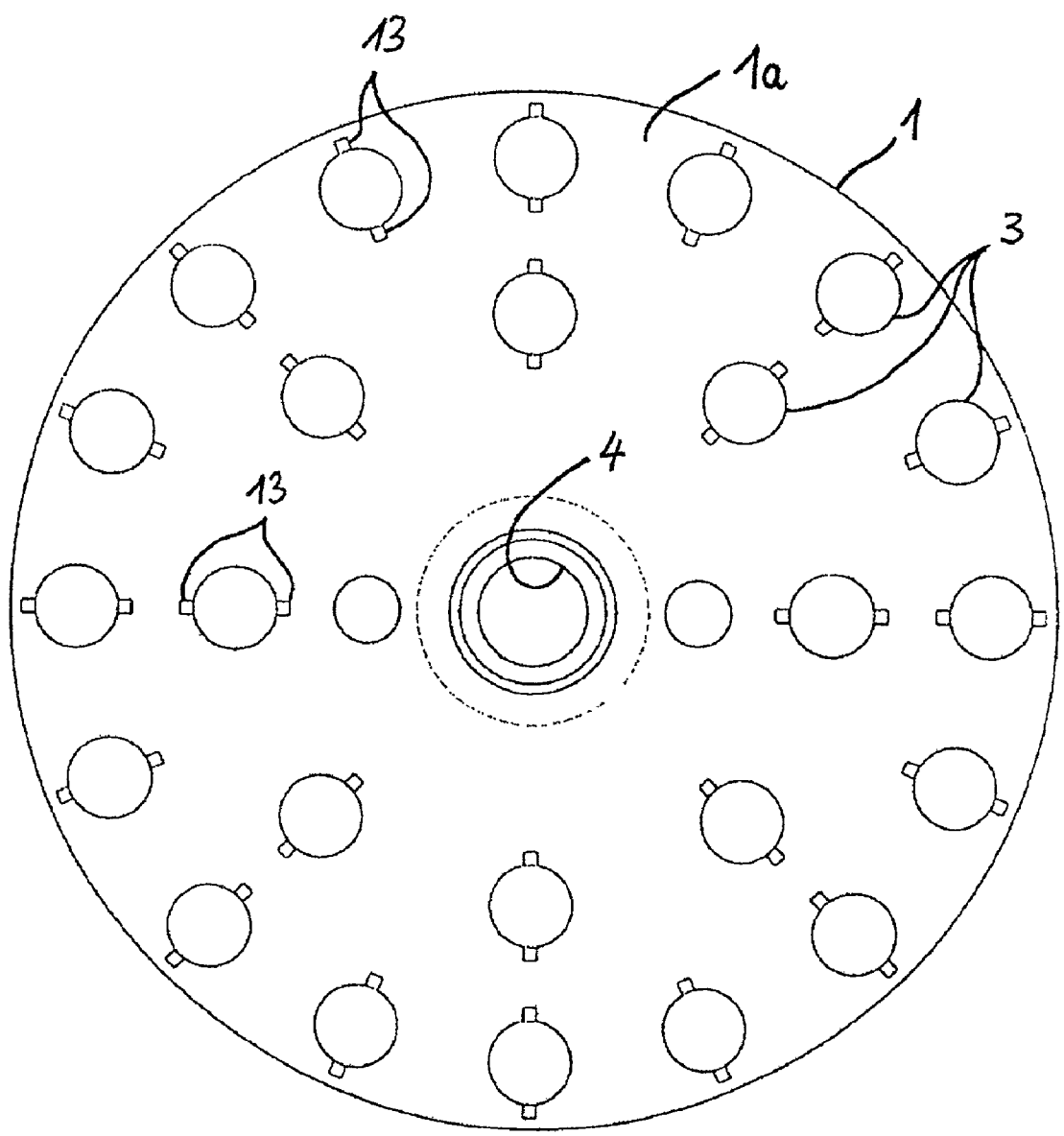
FIG. 2 shows, in a detail view, the configuration of the insert for holding the SCSs.

FIG. 2 shows, in a detail view, the configuration of insert 1 for holding SCSs 2. In this exemplary embodiment, orifices 3 in insert 1 are circular in shape. This is not to be construed as a limitation. Configured at the periphery of a circular orifice 3 are oppositely located notches 13 that ultimately serve to receive and hold SCSs 2. Orifices 3 are arranged around central opening 4.

Figure 3:
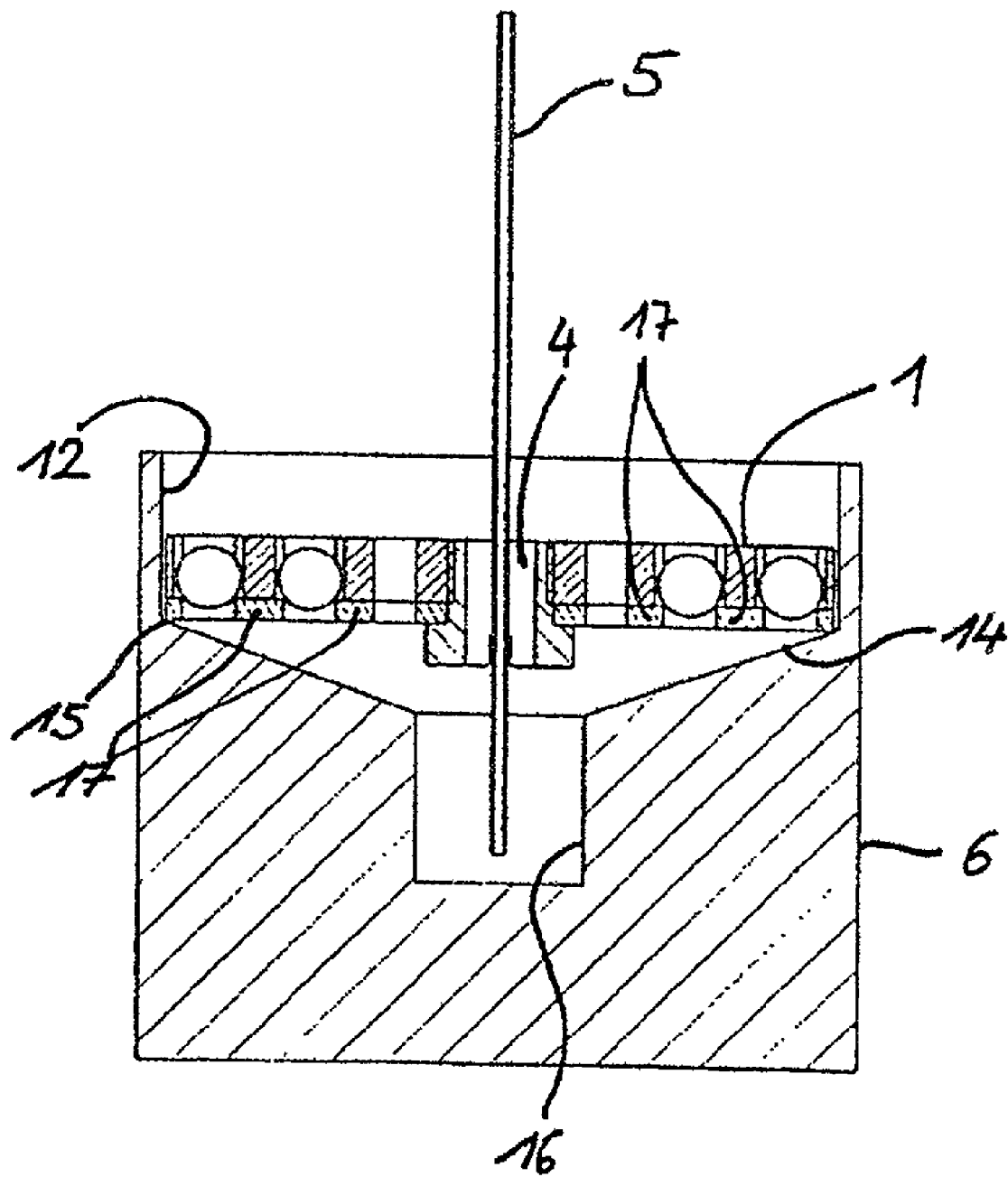
FIG. 3 is a cross section through the container for receiving the insert having SCSs.

FIG. 3 shows, in cross section, container 6 into which insert 1 with SCSs 2 is inserted. Container 6 is made up of a solid, highly thermally conductive block. Circular receptacle 12, adjoining which is a conical diminution 14, is configured in the container. Conical diminution 14 is configured in such a way that it constitutes a stop 15 for insert 1. When insert 1 is inserted, its central opening 4 is arranged above cup-shaped depression 16. As depicted in FIG. 3, hollow needle 5 can be guided through central opening 4 and ends in central cup-shaped depression 16. Insert 1 possesses, at each orifice 3, at least one stop 17 which, when insert 1 is inserted, prevents SCSs 2 from falling out in the direction of central cup-shaped depression 16.

Figure 4:
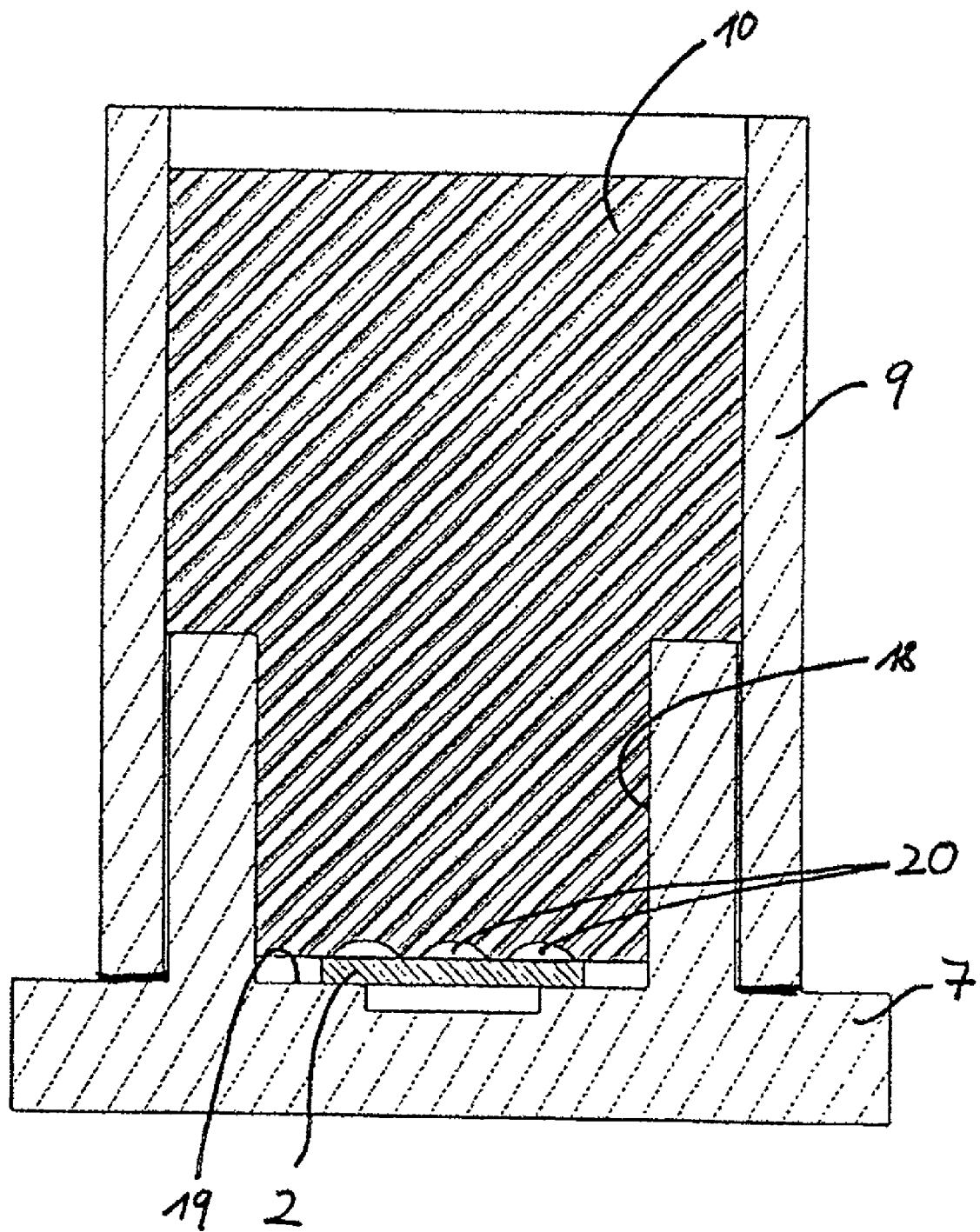
FIG. 4 shows an exemplary embodiment of an embedding mold.
Figure 5:
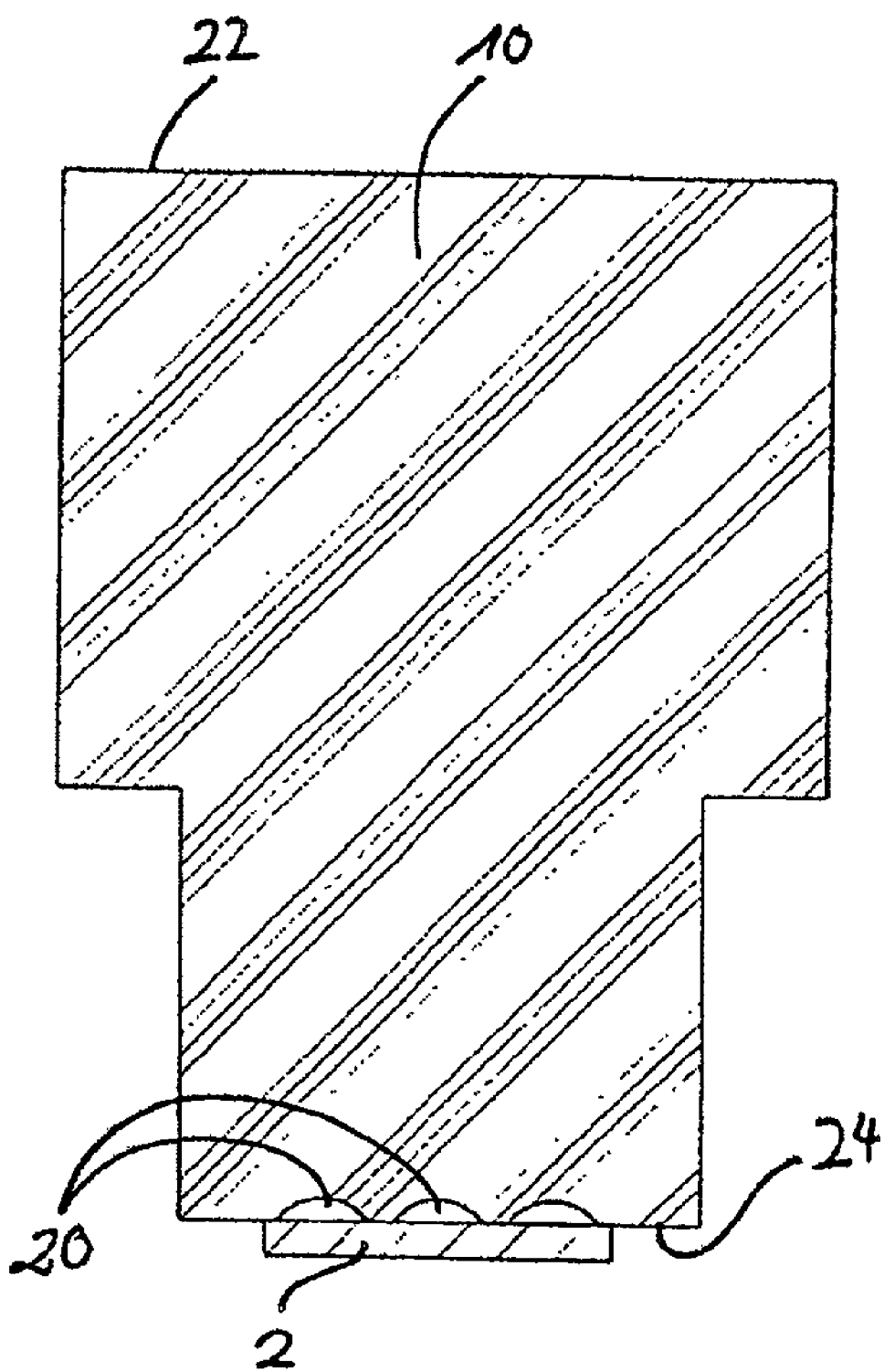
FIG. 5 is a schematic depiction after the embedding mold has been removed from the embedding material.

After completion of the treatment of the cellular monolayers on SCSs 2, a low-temperature embedding step is preferably added. FIG. 4 schematically depicts a portion of an embedding mold, commercially available Eppendorf vessels being used as the embedding mold. Cap 7 of the Eppendorf vessel has a recess 18 into which an SCS 2 is placed in such a way that cellular monolayer 20 present on SCS 2 faces away from base 19 of the cap. A cut-off end 9 of the Eppendorf vessel can be placed onto cap 7. This allows sufficient space above cellular monolayer 20 so that pre-cooled embedding medium 10 can be placed therein. Polymerization of embedding medium 10 occurs under UV irradiation. After curing of embedding medium 10, the temperature is raised to ambient. As seen in FIG. 5, after removal of cap 7, the cured block 22 is pushed out of cut-off end 9 of the Eppendorf vessel. Cellular monolayer 20, which is still covered by SCS 2, is present at end 24 of block 22. In the next process step, SCS 2 is popped off from end 24. This is done by brief immersion in liquid nitrogen; as a result of the mechanical stressed that build up, SCS 2 can be detached particularly easily. Cellular monolayer 20, however, remains in embedding medium 10 at the desired end 24. The production of sections for examinations of cellular monolayer 20 under the electron microscope is existing art.

Figure 6:
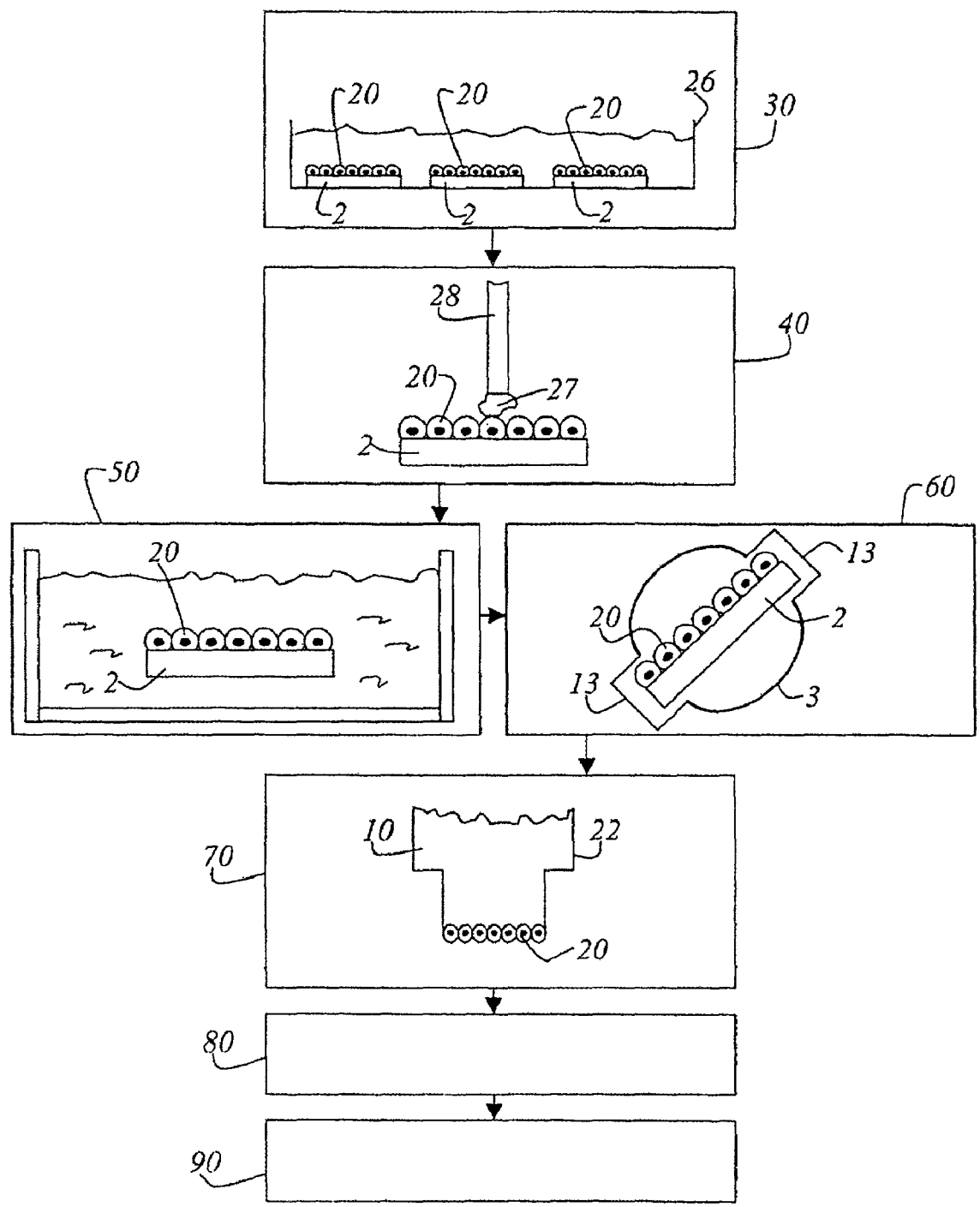
FIG. 6 is a schematic depiction of the method for the preparation of cellular monolayers.

FIG. 6 schematically depicts the method for preparation of a cellular monolayer 20. Culturing 30 of monolayers 20 of cells on SCSs 2 is accomplished in a conventional tissue culture dish 26. For subsequent examination, monolayer 20 of cells, or at least a portion thereof, must be removed from tissue culture dish 26. For that purpose, at least one SCS 2 was already introduced into tissue culture dish 26 before production of monolayers 20 of cells. To begin with, a certain number of SCSs 2 is placed into tissue culture dish 26. It is important in this context that SCSs 2 be carefully cleaned and sterilized. The tissue cultures and an appropriate nutrient liquid are then introduced into tissue culture dish 26. It is particularly important in this context to check that SCSs 2 do not begin to float in the nutrient liquid. The suspension of tissue cultures is deposited onto SCSs 2 in the nutrient liquid. The growth of cellular monolayer 20 on SCSs 2 is monitored with a light microscope (not depicted). When SCS 2 is 70%-80% covered, SCS 2 can be removed together with cellular monolayer 20 from tissue culture dish 26. Removal of SCS 2 is accomplished with a forceps, and drying is performed with filter paper.

A micropipette tip 28, or another sharp-pointed object with low thermal conductivity, is equipped with grease 27 (e.g. Vaseline). Removal 40 of SCS 2 from the filter paper is accomplished using the grease. In the center of SCS 2, SCS 2 is touched on the cell layer with grease 27 on micropipette tip 28, and adheres. SCS 2 is transferred to freezing step 50. Liquid ethane is used, as is known, for freezing 50. As a liquid close to its melting point of approx. −183° C., ethane has the property of rapidly withdrawing heat from the immersed SCS 2. Rapid cooling rates are necessary in order to minimize ice crystal formation in aqueous specimens, such as cellular monolayers 20. In this application, SCS 2 is immersed parallel to liquid surface 34 of the ethane, cellular monolayer 20 facing away from the ethane. This has the advantage that cellular monolayer 20 is protected upon immersion of SCS 2. The reduction in cooling rate is very small, since sapphire possesses good thermal conductivity. Immersion of SCS 2 perpendicular to the surface of the coolant medium yields poor results in specimens with good thermal conductivity, since upon first contact with the coolant medium, parts of SCS 2 that have not yet been immersed are already being pre-cooled.

The cooled SCSs 2 are transferred into the CSS without allowing their temperature to rise above −100° C. Each SCS 2 is introduced vertically into an orifice 3 of the insert. Insert 1 and container 6 are then assembled and transferred into the CSS for further treatment of cellular monolayers 20 on SCSs 2. As already described in FIG. 1, upon substitution 60 of the water in the cells of cellular monolayer 20, various media that substitute for the water in the cells of cellular monolayer 20 are delivered to container 6.

After the completion of substitution 60, low-temperature embedding is performed; from this, the user obtains a cured block 22 at whose end 24 cellular monolayer 20 is located. Curing 70 is performed with UV light. Production 80 of thin sections of cellular monolayer 20 can then be commenced as the next step. Since cellular monolayer 20 is arranged directly at the end, sectioning immediately yields usable thin sections for subsequent electron-microscope examination 90. The preparation method just described makes it possible to obtain, immediately at the beginning of thin-section production 80, usable thin sections for microscopic examination 90.

The tables below present exemplary embodiments for the preparation of cellular monolayers 20. Additions of uranyl acetate (UA), $OSO_4$, and glutaraldehyde (GA) serve to stabilize and enhance the contrast of the cells, and can be added to the substitution medium (methanol or acetone).

A) Substituting water in the cells of the cellular monolayer with methanol containing 0.5 vol % uranyl acetate (UA).

| Process step | Reagent | Time (min.) | Temperature (° C.) | Slope |
|---|---|---|---|---|
| Begin substitution | Methanol containing 0.5 vol % UA | 12 | −85 | |
| Change temperature | | 9 | to −40 | +5 |
| Temperature equilibrium | | 30 | −40 | |
| Substitute | Mixture of 3 parts and 1 part for 60 min. Mixture of 2 parts and 1 part for 60 min. Mixture of 1 part and 1 part for 60 min. | 180 | −40 | |
| Introduce embedding medium | Lowicryl HM20 | 4 | −40 | |
| Cure | Irradiate Lowicryl HM20 with UV light | 36 | −40 | |

B) Substituting water in the cells of the cellular monolayer with acetone containing 0.5 vol % uranyl acetate (UA), 2 vol % $OSO_4$, and 0.25 vol % GA.

| Process step | Reagent | Time (min.) | Temperature (° C.) | Slope |
|---|---|---|---|---|
| Begin substitution | Acetone containing 0.5 vol % uranyl acetate (UA), 2 vol % $OsO_4$, and 0.25 vol % GA | 12 | −90 | |
| Change temperature | | 6 | to −60 | +5 |
| Temperature equilibrium | | 2 | −60 | |
| Change temperature | | 2 | to −20 | +20 |
| Temperature equilibrium | | 2 | −20 | |
| Introduce embedding medium | Epon 812, Spurrs, and Araldite | 30 | +4 | |

C) Substituting water in the cells of the cellular monolayer with acetone containing 0.5 vol % uranyl acetate (UA) and 2 vol % $OSO_4$

| Process step | Reagent | Time (min.) | Temperature (° C.) | Slope |
|---|---|---|---|---|
| Begin substitution | Acetone containing 0.5 vol % uranyl acetate (UA) and 2 vol % $OsO_4$ | 12 | −90 | |
| Change temperature | | 6 | to −60 | +5 |
| Temperature equilibrium | | 2 | −60 | |
| Change temperature | | 2 | to −20 | +20 |
| Temperature equilibrium | | 2 | −20 | |
| Introduce embedding medium | Epon 812, Spurrs, and Araldite | 30 | +4 | |

The invention was described with reference to a particular embodiment. It is self-evident, however, that changes and modifications can be made without thereby leaving the range of protection of the following claims.

What is claimed is:

1. A method for preparing monolayers of cells, comprising the following steps:
    culturing a cellular monolayer on at least one sapphire coverslip (SCS);
    cooling each SCS together with the cellular monolayer in such a way that the formation of ice crystals in the cells of the monolayer is avoided;
    substituting the cellular water in the cells of the monolayer with a suitable medium;
    embedding the cellular monolayer together with the SCS in such a way that the cells of the cellular monolayer on the SCS are surrounded by embedding material, and the SCS is substantially free of embedding material;
    curing the embedding material by irradiation with light of a suitable wavelength;
    cooling the cured embedding material together with the embedded cellular monolayer on the SCS; and,
    popping the SCS off from the embedding material.

2. The method as defined in claim 1, wherein the substitution is performed in a cryosubstitution system; and each SCS with the cellular monolayer is introduced into a container using an insert (1) and wherein the container is inserted into the cryosubstitution system.

3. The method as defined in claim 2, wherein the insert defines a surface and the insert comprises a central opening through which, via a hollow needle, the container in the cryosubstitution system can be filled with an appropriate medium so that substitution of the water in the cells of the cellular monolayer can be performed.

4. The method as defined in claim 3, wherein substitution of the water in the cells of the cellular monolayer is performed using methanol or acetone.

* * * * *